United States Patent [19]

McCauley

[11] 4,182,034

[45] Jan. 8, 1980

[54] PERMANENT DENTURE PLATES AND METHOD OF INSTALLING

[76] Inventor: Margaret McCauley, 314 Alfred Ave., Rome, Ga. 30161

[21] Appl. No.: 831,370

[22] Filed: Sep. 8, 1977

[51] Int. Cl.² ............................................. A61C 13/00
[52] U.S. Cl. .................................................... 433/174
[58] Field of Search .......................... 32/2, 5, 6, 10 A; 3/1.5

[56] References Cited

U.S. PATENT DOCUMENTS

| | | | |
|---|---|---|---|
| 2,836,890 | 6/1958 | Silvis | 32/2 |
| 3,503,079 | 3/1970 | Smith | 3/1.5 |
| 3,514,859 | 6/1970 | Peterson | 32/2 |

*Primary Examiner*—Robert Peshock

*Attorney, Agent, or Firm*—Newton, Hopkins & Ormsby

[57] ABSTRACT

Following the making of a dental impression and the subsequent making of a denture plate, upper plate, lower plate or both, the remaining natural teeth are extracted and the gum or gums are incised along the dental arch. The skirt portions of the plate are placed in the incisions and the plate may be firmly anchored to the jaw bone with screws or the like. The gum flaps formed by the incisions are then sutured to the skirt portions of the denture plate with dissolvable denture material. The suture passes transversely through the gum tissue and gum flaps above the jaw bone and through receiver apertures provided in the skirt portions of the denture plate. The invention is adaptable to complete or partial plates, upper and lower.

4 Claims, 4 Drawing Figures

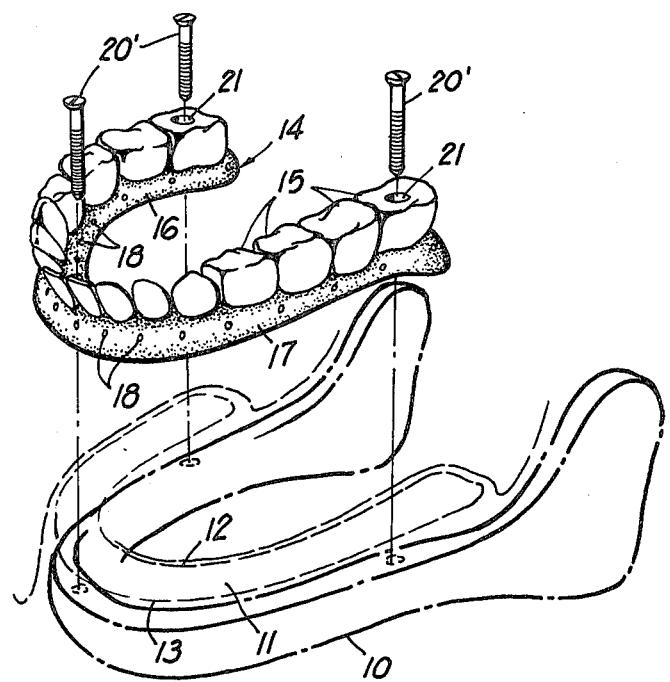
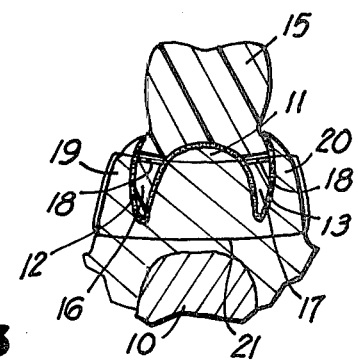
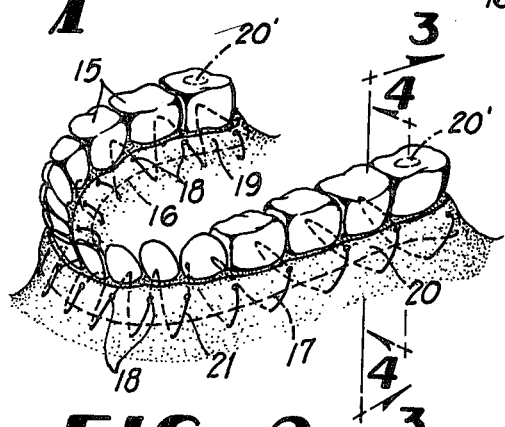
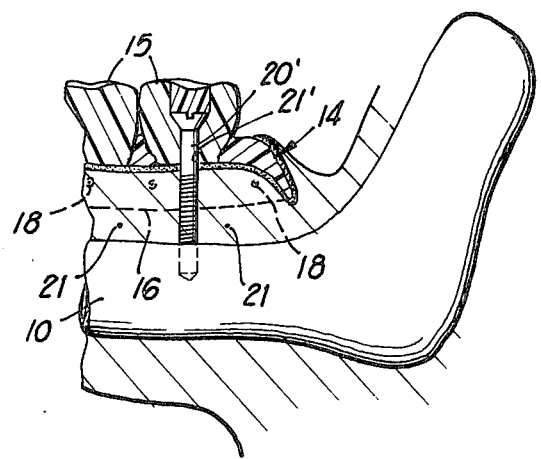
FIG 1
FIG 3
FIG 2
FIG 4

PERMANENT DENTURE PLATES AND METHOD OF INSTALLING

BACKGROUND OF THE INVENTION

Proposals have been made in the prior art relating to permanently installed denture plates and implanted teeth. Some examples of the patented prior art are contained in the following U.S. Pat. Nos.: 973,343; 3,514,858; 1,060,568; 3,624,904; 2,836,890; 3,675,327.

The prior art techniques for permanently installed dentures have not proven entirely practical and satisfactory and thus the concept is not widely utilized at the present time. A main deficiency of the prior art lies in the seating of the denture plate on the top (or bottom) of the gum surface and relying on pins or screws penetrating into the underlying bone structure for anchorage. In time, these anchoring means loosen and the denture plate is no longer secure.

The objective of this invention is to improve on the prior art through provision of a permanent denture plate (complete or partial, upper or lower) and surgical method of installing, in which the plate is not only anchored to the bone structure by screws but has tissue compatible apertured skirt portions which are inserted in gum incisions and sutured in place with dissolvable sutures. The gum flaps formed by incising the gum will heal around the skirt portions of the plate and will permanently and securely retain the plate seated on and within the gum in a much more stable manner than is possible in the prior art.

BRIEF DESCRIPTION OF THE DRAWINGS

FIG. 1 is an exploded perspective view of a denture plate and anchoring screws in relation to the lower gum and jaw bone which are shown in phantom lines.

FIG. 2 is a perspective view of the permanently installed denture plate according to the method embodied in the invention.

FIG. 3 is an enlarged transverse vertical section taken on line 3—3 of FIG. 2.

FIG. 4 is an enlarged fragmentary vertical section taken on line 4—4 of FIG. 2.

DETAILED DESCRIPTION

Referring to the drawings in detail wherein like numerals designate like parts, the numeral 10 designates the lower jaw bone above which the gum tissue 11 is situated. The drawings illustrate the lower gum with all natural teeth removed therefrom and with two parallel incisions 12 and 13 formed by the surgeon along the dental arch in the top of the lower gum. Such incisions would be similarly formed in the bottom of the upper gum where an upper plate according to the invention is being installed. As stated previously, such plates may be complete or partial, as the method and principle of the invention remains unchanged.

Following the preliminary steps of making an impression of the proper gum areas, a denture plate 14 is made by known techniques with suitable artificial teeth 15 mounted therein. As best shown in FIG. 3, the body of the denture plate 14 which follows the dental arch is roughly inverted U-shaped in cross section including dependent lingual and distal skirt portions 16 and 17. At least these skirt portions 16 and 17 are constructed of tissue-compatible materials of a well known type used in implantation dentistry.

The plate 14 is further provided near the tops of skirt portions 16 and 17, between the artificial teeth and near and below the gum line, with spaced suture apertures 18 whose use will soon be described.

The denture plate is next fitted by the surgeon into the patient's gum by forcing the relatively thin skirt portions 16 and 17 downwardly in the gum incisions 12 and 13, FIG. 3, thereby embedding the skirt portions rather deeply in the gum with lingual and distal gum flaps 19 and 20 disposed outwardly of the skirt portions 16 and 17 and the main body of gum tissue 11 filling the channel cavity of the denture plate 14 between its skirt portions 16 and 17.

After the plate 14 is thus seated in the gum tissue, it is anchored in place preferably by passing three anchor screws 20' through prepared openings 21' in the plate and firmly engaging the screws in the underlying jaw bone 10, as best shown in FIG. 4. The screws 20' are preferably arranged in a triangular array, as shown.

Following this procedure, a dissolvable suture 21 is passed through the two gum flaps 19 and 20 and through the apertures 18 of skirt portions 16 and 17, FIG. 3, and through the intervening gum tissue 11. The suture is then looped downwardly below the skirt portions 16 and 17 and again passed transversely through the gum above the bone structure 10 to form anchoring loops of suture material. The suture 21 may be continuous as shown in FIG. 2 to form a multiplicity of connected spiral-like anchoring loops through the apertures 18 of the plate and through the gum tissue at two vertical locations. Separate anchoring loops of dissolvable suture material could be utilized by the surgeon instead of the continuous suture 21, if preferred.

Any suitable infection inhibiting preparation may be applied by the surgeon around the installed plate and incised gum area.

With the passage of time, the gum will knit or heal around the implanted skirt portions 16 and 17 of the plate, and the latter will be permanently anchored not only by the screws or equivalent mechanical fasteners but entirely around the lingual and distal margins of the plate 14 in a nearly natural manner, thus rendering the plate very secure on a permanent basis.

The advantages of the invention over the known prior art should now be readily apparent to those skilled in the art.

It is to be understood that the form of the invention herewith shown and described is to be taken as a preferred example of the same, and that various changes in the shape, size and arrangement of parts may be resorted to, without departing from the spirit of the invention or scope of the subjoined claims.

I claim:

1. A method of permanently installing a denture plate having laterally spaced skirt portions and said plate being provided with suture openings in spaced relation along the dental arch comprising the steps of incising a toothless gum along two spaced incision lines following the dental arch, inserting the skirt portions of said plate into said incisions until the skirt portions are substantially embedded in the gum and the plate is firmly seated against the gum, and then passing loops of dissolvable suture material through said openings and through the natural gum transversely.

2. The method of claim 1, and passing said loops of dissolvable suture material by utilization of a continuous strand of suture material to form plural spaced suture loops along the dental arch in spaced planes which are generally normal to the gum plane.

3. The method of claim 1, and additionally anchoring said denture plate by inserting mechanical fastener elements therethrough and engaging the mechanical fastener elements with adjacent bone structure.

4. The method of claim 1 wherein said loops have top sections at the elevation of said opening and bottom sections beneath said skirt portions.

* * * * *